US 6,493,090 B1

(12) United States Patent
Lading et al.

(10) Patent No.: US 6,493,090 B1
(45) Date of Patent: Dec. 10, 2002

(54) DETECTION OF A SUBSTANCE BY REFRACTIVE INDEX CHANGE

(75) Inventors: Lars Lading, Roskilde (DK); Lars Lindvold, Kokkedal (DK)

(73) Assignee: Torsana A/S, Skodsborg (DK)

( * ) Notice: Subject to any disclaimer, the term of this patent is extended or adjusted under 35 U.S.C. 154(b) by 133 days.

(21) Appl. No.: 09/624,891

(22) Filed: Jul. 24, 2000

(51) Int. Cl.[7] .................................................. G01B 9/02
(52) U.S. Cl. ...................................... 356/484; 356/480
(58) Field of Search ................................. 356/481, 480, 356/484; 385/12, 14; 250/227.19, 227.27, 227.18

(56) References Cited

U.S. PATENT DOCUMENTS

| | | | |
|---|---|---|---|
| 4,325,635 A | 4/1982 | Sattler et al. | |
| 4,553,841 A | 11/1985 | Coppa et al. | |
| 5,437,840 A | 8/1995 | King et al. | |
| 5,448,657 A | 9/1995 | Kim et al. | |
| 5,465,151 A | * 11/1995 | Wybourne et al. | 356/481 |
| 5,514,596 A | 5/1996 | King et al. | |
| 5,564,832 A | 10/1996 | Ball et al. | |
| 5,766,956 A | 6/1998 | Groger et al. | |
| 5,793,485 A | 8/1998 | Gourley | |

OTHER PUBLICATIONS

P. L. Gourley and A. E. McDonald, "Semiconductor microlasers with intracavity microfluidics for biomedical applications," SPIE, vol. 2978.pp. 186–196 (1997).

O. Hennig et al., "Distributed Bragg reflector laser–based sensor for chemical detection," Optics Communications, Nov. 15, 1998, 311–315.

S. Kubitschko et al., "Sensitivity Enhancement of Optical Immunosensors with Nanoparticles," Analytical Biochemistry 253, 112–122, Article No. AB972337, 1997.

Otto S. Wolfbeis, "Capillary waveguide sensors," Trends in Analytical Chemistry, vol. 15, No. 6, 1996.

Maria–Pilar Marco et al., "Environmental applications of analytical biosensors," Meas. Sci. Technol. 7, 1547–1562, 1996.

A. Brecht et al., "Optical porbes and transducers," Biosensors & Bioelectronics 10, 923–936, 1995.

A. H. Severs et al., "Enhanced surface plasmon resonance inhibition test (ESPRIT) using latex particles," Biosensors & Bioelectronics 8, 365–370, 1993.

Horst Weber, "Laser Grundlagen und Anwendungen," (1972).

A. Ding et al., "Messung geringer Elekronendichten in Plasmen," (1968).

* cited by examiner

Primary Examiner—Samuel A. Turner
Assistant Examiner—Patrick Gonnolly
(74) Attorney, Agent, or Firm—Jones, Tullar & Cooper PC

(57) ABSTRACT

A sensitive refractive index based detector comprises a first laser cavity (7) and a second laser cavity (7') each for generating a respective laser light beam. Each laser cavity is defined in a planar waveguide. The surface of the waveguide of the first laser (7) receives a sample to be detected. Light from the two lasers is mixed using a coupling grating (3) and a beat frequency between the lasers dependent upon the refractive index of the substance is measured at a detector (4). Extremely sensitive measurement of small quantities of substance are made possible.

21 Claims, 3 Drawing Sheets

DETECTION OF A SUBSTANCE BY REFRACTIVE INDEX CHANGE

CROSS REFERENCE TO RELATED APPLICATIONS

Figure 1:
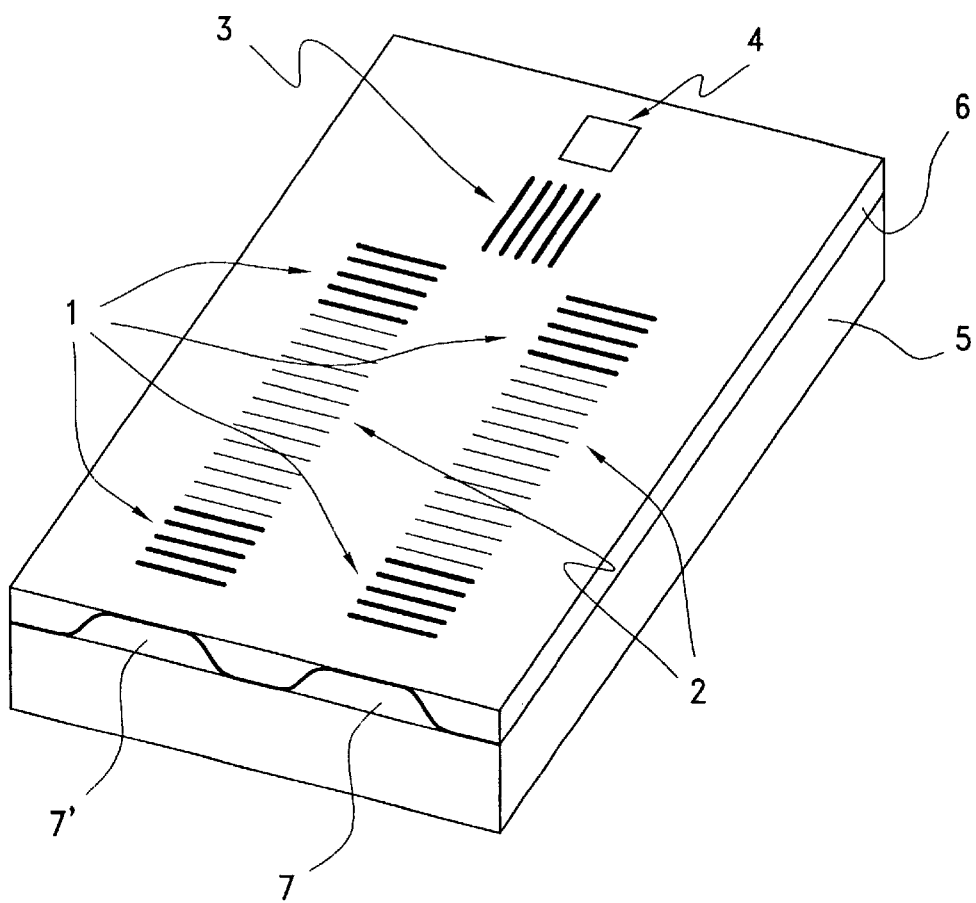

This application claims the benefit under 35 U.S.C. §120, of International Application Number PCT/EP99/00401, which was filed on Jan. 22, 1999 and designates the United States.

The present invention relates to a method and an apparatus for sensing the presence, concentration or amount of a substance through detection of a change in refractive index caused by said substance.

In particular, the present invention includes such methods and apparatus for determination of the presence, concentration, or amount of a substance, such as a fluid, in which the refractive index of the fluid is a function of the concentration of one or more chemical species in the fluid. The invention has applicability particularly in the field of clinical analysis, but also, for example, in wet chemical analysis in general, and in gas analysis.

Detection of minute concentrations of chemical species, such as bioactive molecules, is presently typically based on affinity reactions, such as antigen—antibody (immunoassay) reactions, hormone—receptor reactions, DNA/RNA—complimentary string reactions, reactions with cavitands, i.e. cyclic saturated hydrocarbons for selective binding of ions or molecules, such as glucose, or catalytic reactions, such as enzyme- substrate/inhibitor/co-factor reactions.

These reactions facilitate recognition of individual molecules of a substance thereby making identification of substances at very low concentrations, typically at the order of $10^{-12}$ mol/L, possible.

The attractive properties of known detection techniques based on the above-mentioned reactions are high specificity as well as sensitivity to the analyte in the presence of other substances. This means that bioassays based on these methods can be performed, e.g. utilizing biosensors, in samples of body fluids (e.g. whole blood, serum, saliva and urine) whereby time and labor consuming purification steps can be avoided.

Assays based on the above mentioned binding mechanisms, typically employ luminescent detection principles, such as fluorescence, bioluminescence, or chemiluminescence, for detection of the presence of specific chemical species. Luminescent techniques are widely used in assays involving "wet" chemistry, such as assays employing microtitre plates or flow cytometry.

It is known to detect the presence of a specific chemical species by immobilization at a surface of a reagent comprising antibodies or antigens, and bringing an analyte containing the species to be detected into contact with the reagent. The reagent may for example be immobilized at an inner surface of a microflow channel in which the analyte flows. As an affinity or catalytic reaction takes place between the species to be detected and the reagent, the refractive index at the surface bearing the reagent changes and thus, the presence of the species can be detected by detection of the change in refractive index. This change typically ranges from $10^{-7}$ to $10^{-4}$.

It is also known to detect changes in the refractive index of thin layers of substance by evanescent wave sensing.

A comprehensive review of optical devices for biosensing based on this technique has been disclosed in A. Brecht et al. "Optical Probes and Transducers", Biosensors & Bioelectronics, 10, pp. 923–936, 1995 (Ref. 1).

Surface plasmon resonance detection as in for instance Ref. 1 relies on the excitation of a surface plasmon in a thin metal film, typically at a glass-liquid interface. This technique uses the evanescent field which has an exponentially decaying field component along the normal to the glass-liquid interface. With an analyte present at the upper boundary of the metal-liquid interface the refractive index in this region is modified causing a change in the resonance surface plasmon excitation angle. This change in angle is a measure for the refractive index change—and consequently the chemical composition of the analyte.

Evanescent waves are intricately associated with propagation of light in waveguides. A wave travelling along the core of a waveguide, be it an optical fibre or planar waveguide, will generate an exponentially decaying field that extends into the cladding of the waveguide. The penetration depth $d_{ew}$ of this tail into the cladding depends on the difference between the refractive indices of the core and the cladding such that a large difference in the refractive indices implies a short penetration depth.

The penetration depth ranges from a fraction of the optical wavelength to many wavelengths depending on the specific waveguide parameters.

The evanescent wave, can be used as a means for both excitation and detection of a layer adjacent to the cladding of the waveguide provided that the thickness of the cladding is smaller than the penetration depth $_{ew}$ of the corresponding evanescent wave. In the case of excitation, the most well-known method is evanescent wave excitation of fluorescence in capillary waveguides, see e.g. O. S. Wolfbeis in Trends in Analytical Chemistry 15 pp. 225–232, 1996 (Ref. 2). In this application, the use of evanescent waves makes it possible to selectively excite a thin fluorescent labelled detection layer but not the bulk analyte.

Fibre optic biosensors (see e.g. M-P. Marco et al. in Meas. Sci. Tech. 7, pp. 1547–1582, 1996) (Ref. 3) use the evanescent field generated in the cladding of a single-mode optical fibre due to total internal reflection generated at the inner boundary of the fibre core. When molecules with an appropriate excitation energy are located in the evanescent field, they absorb energy leading to an attenuation in the reflected light inside the fibre core. To get a reasonable sensitivity the molecules are typically labelled with e.g. a fluorescent dye so that the molecules are able to re-emit at a longer wavelength (lower energy) as fluorescence after being excited by the evanescent field. Part of the re-emitted light is coupled back into The fibre core and propagates towards the end of the fibre before being detected by a photodetector.

Within the field of integrated optics biosensors may also be implemented. Integrated optics facilitates the possibility of making more device-like biosensors like interferometric sensors (e.g. a Mach Zehnder interferometer) which rely on the detection of an induced phase change between a sensing arm and a reference arm, see Ref. 3. The biological interaction expressed as a phase change between the light beam in the sensing arm and the reference arm is detected by standard interferometric means.

Further, it is known to detect changes in the refractive index of thin layers of substance by intracavity sensing.

In Gourley et al. "Semiconductor micro lasers with intracavity microfluidics for biomedical applications", Proc. SPIE, Vol. 2987, pp. 186–196 (1997) (Ref. 4), a method is disclosed in which a cell, e.g. an erythrocyte, is introduced into the cavity of a vertical cavity surface-emitting laser (VCSEL). Due to the fact, that the cell does not absorb at the wavelength of the GaAs laser (850 nm), the cell in the cavity will act as a Fabry-Perot etalon. Abnormalities in the structure of the cell-membrane, like Sickle-cell anaemia of blood-cells, will cause higher order transverse modes to be generated. These modes can be detected by a suitable solid state imaging device, such as a CCD.

In U.S. Pat. Nos. 5,437,840 and 5,514,596 (Refs. 5,6) an apparatus and method for intracavity sensing of macroscopic properties of chemicals are disclosed. The apparatus comprises an optical resonator that is pumped by a light source that may be positioned inside or outside the optical resonator. A reflective element having a surface is positioned inside the optical resonator so that total reflection of the mode excited within the resonator is provided. A detector for measuring the resonator output is positioned outside the resonator. As the substance to be analyzed is introduced in the evanescent field region at the outer surface of the reflective member, the refractive index at the surface changes causing the resonance frequency of the optical resonator to change accordingly. In some embodiments, this change in resonant frequency is measured. In most embodiments however, fluorescence of a label at the surface is sensed. The change in resonant frequency of the resonator may be sensed using a conventional scanning Fabry-Perot interferometer as a sensor.

The resonator may take the form of a fibre laser having a sensing region formed by the removal of the cladding of the fibre. Fluorescence stimulated in the sensing region may be detected.

U.S. Pat. No. 5,766,956 (Ref. 7) published after our priority date, discloses incorporating a waveguide laser into the surface of a substrate, with detection of a substance received on the surface of the device causing a change in wavelength of the laser light which is detected using an interferometer.

It is a disadvantage of these known methods and apparatus that in order to be able to detect chemicals in minute concentrations, the resonance frequency of the optical resonator has to be accurately determined.

It is another disadvantage of these known methods and apparatus that precise temperature control of the cavity is needed to be able to determine changes in resonance frequency accurately.

"Laser-Grundlagen und Anwendendungen" by Weber and Herziger published by Physik Verlag (Ref. 8) discloses at page 190 the use of two similar gas lasers in a device in which the frequency difference between the two lasers is measured as a beat signal. An object to be measured can be introduced into the cavity of one such laser and its effect on the frequency of the laser may be measured by its effect on said beat frequency. It is said that using such apparatus one may measure the electron density in a plasma. A related disclosure is provided in Ding, Hertziger & Weber, Z. F. Angew. Phys. 1968, Bd.25, Heft 3, 168–171 (Ref. 9).

U.S. Pat. No. 5,564,832 (Ref. 10) discloses a chemical sensor in which laser light is propagated in a birefringent fibre laser as two orthogonal polarised modes of differing frequency, one of which is more affected than the other by the presence of a substance to be sensed on the outside of the fibre. A change in the beating between the two modes is used as a sensitive method of detecting the presence of the said substance. For compensation against temperature changes, two lasers may be used in the same general area, one being exposed to the substance and the other not. It appears to be intended here that the beat frequency between the two modes of each of the two lasers should be recorded and that mathematically, changes in the beat frequency of the second laser should be subtracted from those of the first laser to achieve temperature compensation. No optical beating between the two lasers is proposed therefore.

We have appreciated that the teaching of U.S. Pat. No. 5,564,832 relating to chemical sensing is unworkable because for the substance to be sensed to affect the propagation constant of one of the modes, the substance will have to be brought within the evanescent wave of the light at the total internal reflection boundary between the fibre core and cladding. However, removal of all or most of the cladding to provide access for the substance to this area will so disrupt the birefringent properties of the fibre that the reproducible production of two orthogonal stable propagation modes will be difficult.

Accordingly, we now provide apparatus for sensing the amount, concentration or presence of a substance through a change in refractive index, comprising a first laser having a laser cavity defined by a waveguide for generation of a first laser light beam and a second laser having a laser cavity defined by a waveguide, optionally partially shared by said laser cavity of the first laser, for generation of a second laser light beam, the propagation of said laser light in said first laser cavity being characterised by a first propagation constant and the propagation of said laser light in said second laser cavity being characterised by a second propagation constant, the waveguide defining the first laser cavity having a sensing surface adapted to receive a sample of a substance to be sensed, such that the presence of said substance at said sensing surface alters the said first propagation constant and the frequency of light in said first laser beam, and means for combining said laser beams to produce beating between their respective frequencies and means for detecting a change in the said beating consequent upon a said change in said first propagation constant caused by the presence of said substance.

Henning et al, Optics Communications 156 (1998) 311–315 (Ref. 11) published after our priority date discloses a sensor having two fibre lasers, one sensing and one reference, with heterodyne determination of their frequency difference, as a proposal for detecting acetone vapour.

It is an important advantage of the invention that the difference between the frequencies of the first and second lasers is independent of the actual physical interaction length between the substance and the laser light being influenced by the substance. Instead the effective interaction length is given by the optical propagation length traversed by the light in the laser cavity during the mutual coherence time of the two lasers.

The substance may be a fluid, such as water, dairy products, a body fluid, such as whole blood, serum, saliva, urine, etc, or a gas containing possibly minute concentrations of a chemical species, the concentration of which is to be determined. The species may comprise antigens, antibodies, hormones, DNA strings, RNA strings, or simple molecules, such as glucose.

The laser system may comprise lasers such as gas lasers, such as HeNe lasers, Argon lasers, or Krypton lasers, or solid state lasers, such as semi-conductor lasers, such as GaAs based lasers, InGaAsP based lasers, or InP based lasers, waveguide lasers, such as fibre lasers or polymer lasers.

Each laser may operate in a single mode or may have multiple axial modes with each laser having the same mode spacing.

A laser cavity of the laser system may be constituted by the laser cavity of one or more of the above-mentioned lasers.

A laser cavity of the laser system may be pumped electrically or optically. The laser cavity is adapted to generate at least one predetermined mode, such as the TE00 mode, $TM_{00}$ mode, $TE_{01}$ mode, $TM_{01}$ mode, etc, as is well known in the art.

Preferably, a reagent comprising e.g. antibodies or antigens or other species that specifically will bind chemical species contained in the substance and the concentration of which it is desired to determine is positioned on the sensing surface of the first laser cavity of the laser system. When a sample of the substance is brought into contact with the reagent on the surface of the first laser cavity, the chemical species are bound by the reagent thereby changing the refractive index of the layer containing the reagent and abutting the surface of the first laser cavity and into which evanescent waves generated by the laser light in the first cavity extend. Thereby, the propagation constant of the first laser beam is changed and, thus, varies as a function of the refractive index of the layer at the surface and in turn as a function of the concentration of species bound by the reagent.

It is an important aspect of the present invention that the change in propagation constant is determined by comparison with another propagation constant that substantially does not change with the concentration of species bound by the reagent, or, that changes as a second function of said concentration.

This may be obtained by providing in the laser system the first and second laser cavities, the laser cavities being substantially identical except that the first laser cavity has a sensing surface with the reagent and the second laser cavity has a surface that does not hold the reagent. When a sample of the substance is applied to corresponding surfaces of the laser cavities, the propagation constant of the first laser changes as the chemical species the concentration of which are to be determined are retained at the surface increasing the concentration of the species at the surface with time while the propagation constant of the second laser changes differently as the species are not retained at the surface of the second cavity.

Severs et al in 'Biosensors & Bioelectronics' 8 (1993) 365–370 (Ref. 12) disclose the enhancement of a surface plasmon resonance (SPR) detector by the use of a sandwich format in which antigen on the detector is used to bind an antibody to be detected and the SPR signal is enhanced by binding to the thus bound antibody latex beads coated with antigen. Preferred sizes for the latex beads relative to the evanescent wave penetration depth are disclosed by Kubitschko et al in 'Analytical Biochemistry' 253, 112–122 (1997) (Ref. 13).

Such sandwich formats may also be employed in the practice of the present invention. Thus the sensing surface may be provided with a specific binding partner for a species to be detected and the species, before or after binding to the sensing surface, may be bound to a particulate label, enhancing the change in refractive index produced by binding to said surface. The particulate label, as known in the art, may be a metal nanoparticle, such as colloidal gold, or a mineral particle, such as $TiO_2$, or a latex particle. Such particulate labels if metal particles will generally have a size smaller than the optical wavelength. They may be larger particles in the micrometer or nanometer range of dielectric material.

It is not essential that the sensing surface has a specific affinity for the substance to be detected. This will depend upon circumstances. For instance, such a sensor may be employed to follow the course of a capillary electrophoresis procedure, in which the sensor responds to the presence of molecules, e.g. protein molecules, in the eluate in a non-specific manner.

The refractive index sensing apparatus of the present invention, may form the detector of an electrophoretic or chromatographic separation system for analysis of chemical species in a sample. In electrophoresis and chromatography a sample composed of a mixture of chemical components is resolved into its components and each component is passed in front of a detector to monitor the elution time point and the amount. Electrophoresis is the separation of components in a sample based on the behaviour of molecules in an electrical field. One mode is capillary electrophoresis which includes: capillary zone electrophoresis, isotachophoresis, capillary electrokinetic chromatography, capillary gel electrophoresis and isoelectric focusing (Analytical Chemistry 61:292A–303A). Chromatographic separation can be defined as separation techniques involving mass-transfer between stationary and mobile phases. One chromatographic mode is High Performance Liquid Chromatography (HPLC). HPLC may be classified as: adsorption chromatography including normal and reversed-phase chromatography, ion-exchange chromatography, and size exclusion chromatography.

The development of nanoliter-picoliter optical detectors for capillary separation techniques, such as capillary electrophoresis (CE), is gaining considerable importance in chemical analysis. Several aspects, including speed of analysis, high resolution, and efficiency account for the acceptance of this technique. High electrical fields across the capillary ends force ionic species to migrate through a buffer-filled capillary. The different species travel at different speeds according to their charge, size or both.

Because the separation performance increases with a reduction of the inner diameter (i.d.) of the capillary tube employed in CE separations, there is a need to develop new detectors that are specifically suitable for CE. Sensors according to the invention may similarly be used as HPLC detectors.

Where specific binding partner molecules are provided on the sensing surface they may be of any of the many kinds known in the art. They may be oligonucleotides (RNA or DNA) or synthetic analogues thereof such as PNA. They may be antibodies or fragments thereof with specific binding ability. They may be molecules such as biotin or avidin (or steptavidin) with specific affinity for a chemical binding partner. The binding ability of the surface may be less specific than in these examples. For instance the surface may be hydrophilic or hydrophobic for detecting molecules of opposite affinity, e.g. water as a contaminant in oil.

Alternatively, such specific binding ability as is desired may be an inherent property of the surface itself rather than of any material coated thereon.

The difference between the propagation constants of the first and the second lasers is determined as the frequency difference between light beams emitted from the first and second lasers. The frequency difference is determined utilizing light beating techniques giving direct measurement of the frequency difference.

As frequency difference may be determined with extreme resolution and accuracy, refractive index changes or differences of extremely low magnitudes can be determined by frequency difference determination.

Further, determination of frequency difference eliminates the need for determination of the absolute frequencies of the lasers.

Still further, the need for accurate temperature control encountered when using an individual laser cavity is reduced but preferably one ensures that the two cavities operate at substantially identical temperatures. The temperature may need to be selected to suit the material to be sensed, e.g. to match the temperature range within which a chemical reaction may occur.

A light detector, such as photodiode, or a photo-multiplier tube, may be provided for detection of the frequency difference of the first and the second light beams. Coherent detection across the photo sensitive area of the light detector is required which means that the wavefronts of the light beams must be substantially aligned across the photo sensitive area of the light detector. The light detector generates an electrical output signal that is a function of intensity of light incident upon it and thus, when the first and the second light beams are imposed coherently on its photosensitive area generates an electrical output signal having a component frequency that is identical to the difference between the frequencies of the first and the second light beams.

When the first and second light beams originate from the same cavity and have different polarisation directions, a polarising optical element has to be inserted into the optical path between the light detector and the cavity providing detection of the frequency difference between the first and second light beams at the light detector.

The wavefront alignment may be provided by an optical element, such as a diffraction grating, such as a reflecting diffraction grating or a transmitting diffraction grating, a thin film component, such as a beam-splitter, or a birefringent prism in combination with a polarizing element. The optical element then constitutes a part of the first and second optical means that is positioned in the optical path between the light detector and the laser system.

The optical element may be made of glass, glass ceramics, polymers, semiconductor, metals, or the like.

The first and second optical means, respectively, may comprise one or more optical waveguides, e.g. made of glass, glass ceramics, polymers, a semi-conductor, or the like, for transmission of light between the laser system, the optical element and the light detector.

Further, it is possible to integrate the laser system, optical waveguides, the optical element, the light detector, and electronic integrated circuits into a sensor on a common substrate leading to apparatuses of the above kind of the size of an electronic integrated circuit.

In a preferred embodiment, the sensor comprises a monolithic structure comprising a suitable, mechanically stable substrate.

Further, as the sensor is supported on a suitable, mechanically stable substrate it is obtained that the sensitivity of the sensor to ambient conditions is predominantly determined by the properties of the substrate.

Suitable, mechanically stable substrates may be made of semiconductor, such as Si, GaAs, etc, glass, glass ceramics, polymers, or the like.

In order to obtain an even more compact apparatus, in a preferred embodiment, the sensor elements are incorporated into an integrated opto-electronic element.

Preferably, the integrated opto-electronic element comprises a substrate, and a waveguide comprising the suitable diffracting structures integrated therein or in the interface between the waveguide and the substrate.

The waveguide may consist of any suitable waveguide for integrated opto-electronic elements known in the art.

It is preferred that the waveguide is integrated with the substrate, i.e. either in the surface or in the bulk of the substrate.

In one embodiment it is preferred that the laser system, the light detector, or both, are externally connected to the integrated opto-electronic element.

In another embodiment it is preferred that both the laser system and the light detector are embedded in the opto-electronic element.

Signal processing means to be used according to the invention comprises any suitable signal processing device incorporating frequency determination, timing and/or correlation procedures known in the art.

In a preferred embodiment the signal processing means consist of an integrated signal processor device incorporated into the integrated opto-electronic element.

Below, the performance of the apparatus according to the invention is compared with a system based on a Mach-Zehnder interferometer. The apparatus may achieve a resolution that is $10^4$–$10^6$ higher than the sensitivity of a system based on an external interferometer.

Implementations based on semiconductor materials with a waveguide configuration and Bragg-mirrors is possible with existing technologies. A polymer based configuration may be used.

Devices based on evanescent wave sensing are usually based on some form of integrated optical components where the inter-action region between the sensing layer and the optical circuit is on the order 1 mm$^2$. Consequently if the substance to be analyzed is partly dissolved or suspended in a fluid or contained in an emulsion, the fluid handling in such devices usually is based on microfluidics. Microfluidic systems make it possible to manipulate single cells and study various biochemical reactions under pure diffusion controlled conditions and this makes them very attractive to biomedical research as biosensors.

In one embodiment of the present invention an apparatus and a method is provided in which the propagation constant of a waveguide is changed as a result of a change of the refractive index of the outer layer of a waveguide. The propagation constant can be approximately:

$$\beta = n_e k_0 (1-\Delta) = n_{eff} k_0 \tag{1}$$

where $$k_0 = \frac{2\pi}{\lambda} \tag{2}$$

$$n_e(1-\Delta) = n_{eff}$$

and $$\Delta \cong \frac{n_e - \langle n_c \rangle}{n_e} \tag{3}$$

where $\lambda$ is the free space wavelength, $n_e$ is the refractive index of the core of the waveguide, and $\langle n_c \rangle$ is the effective refractive index of the cladding. The effective refractive index is defined by $$n_{eff} = n_e(1-\Delta) \tag{4}$$

The accuracy (or resolution) is in general given by the actual interaction length normalized by the optical wavelength. This can be illustrated by considering a Mach-Zehnder interferometer.

Consider a Mach-Zehnder interferometer where a small change in the refractive index causes a small change in the optical path length difference. The phase change is $$\Delta\varphi = \frac{2\pi\Delta n_{eff} l}{\lambda} \quad (5)$$

where the refractive index along the path, 1, is $n=n_0+\Delta n$. Thus $$\Delta n_{eff} = \frac{\Delta\varphi\lambda}{2\pi l} \quad (6)$$

We note that for a given minimum detectable phase change a larger waveguide length, l, gives a smaller detectable change of the refractive index. A number of factors, like linearity and noise of the detection circuitry, photon noise and thermal effects may give the minimum detectable phase change.

An example: Let the minimum detectable phase change be $10^{-4}$ radians and let $$\frac{\lambda}{2\pi n_{eff} l} \cong 10^{-4} \quad (7)$$

This gives that $$\frac{\Delta n_{eff}}{\langle n_{eff}\rangle} = 10^{-8} \quad (8)$$

The present invention uses in such embodiments the interaction between a sensing layer immobilized on a waveguide laser.

Consider a laser where the effective refractive index in the cavity is changed by $\Delta n$. This implies a change in the oscillation frequency of the laser given by $$\frac{\Delta n_{eff}}{\langle n_{eff}\rangle} = \frac{\Delta f}{f_0} \quad (9)$$

We note that no interaction length appears in Eq. (10). Very small frequency shift are preferably detected as shifts relative to a stable reference. Light beating is then applied to obtain the difference frequency. The effective interaction length is then given by the optical propagation length within the mutual coherance time of the two lasers.

An example: Let $\Delta f_{min} \sim 100$ Hz and let $f=4\times 10^{14}$ Hz. Thus $$\frac{\Delta n_{eff}}{\langle n_{eff}\rangle} \cong 2.5 \times 10^{-13} \quad (10)$$

Compare equations (8) and (10). The difference is essentially caused by the fact that in this simple analysis the effective interaction length of the laser is implicitly much larger than the actual interaction length l.

The system proposed in the present invention uses two preferably almost identical optical resonators. The frequency spacing should preferably be much smaller than the width of the gain profile in order to avoid the laser frequencies being affected by the gain profile.

The optical wavelength and materials may with respect to the passive parts of the sensor be chosen as for Mach-Zehnder configurations.

In differential systems it is necessary that erroneous perturbations causing optical path length differences between the two lasers are smaller than that caused by the refractive index change to be measured. Temperature gradients may here be most important. The temperature coefficients for the thermal expansion and for the refractive index, respectively, are in general of opposite sign and roughly of the same order of magnitude. However, an exact cancelling is unlikely for materials relevant for the present application. Thus, a very close thermal contact between the structures supporting the two laser beams is desirable.

In a second aspect, the invention provides apparatus for sensing the amount or presence of a substance comprising:

a laser having a laser cavity comprising a free space gain portion for generation of laser light in two mutually orthogonally polarized modes and a bifurcated portion comprising a pair of arms, means for splitting said laser light into two beams each of one said polarisation mode and for directing a respective beam into each of said arms of the bifurcated portion of the cavity, the light of each said polarization mode having a respective frequency, means for allowing a said substance to interact in one said arm with one of said two beams so as to alter the optical length of said arm and hence the frequency of the light of the polarization mode associated with that arm, and means for detecting said change in frequency as a change in a beat frequency component produced by beating of the two said polarization modes.

Thus, in comparison with the disclosure of Ref. 10, the interaction of one polarisation mode preferentially with the substance to be sensed is obtained by arranging for spatial separation of the polarisation modes. This avoids the need to attempt to generate the modes in a birefringent fibre laser. The free space gain region of the laser cavity may be a gas region or a solid state region.

Said bifurcated portion of the laser cavity may also provide free space transmission of light. Alternatively, this portion of the cavity may provide waveguide transmission of light.

Figure 2:
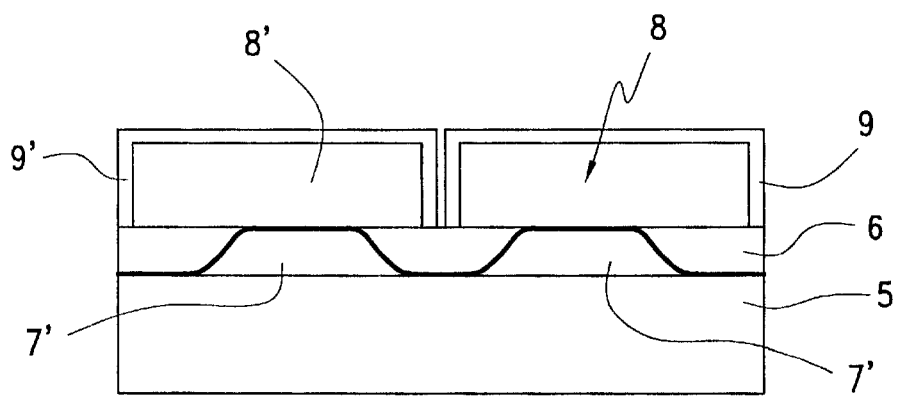
Figure 3:
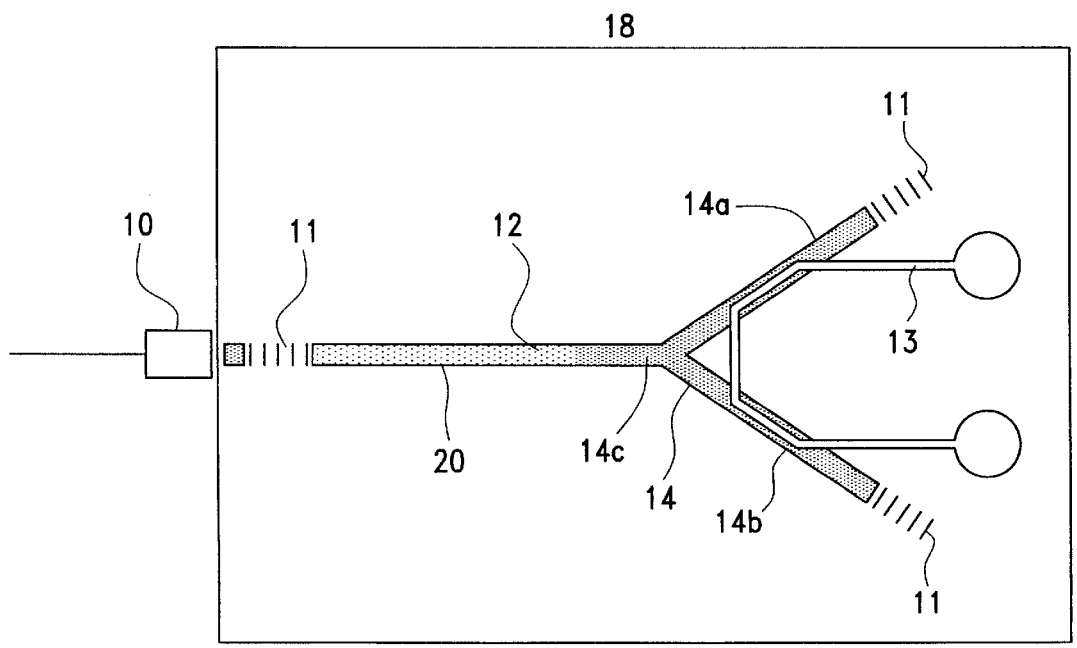
Figure 4:
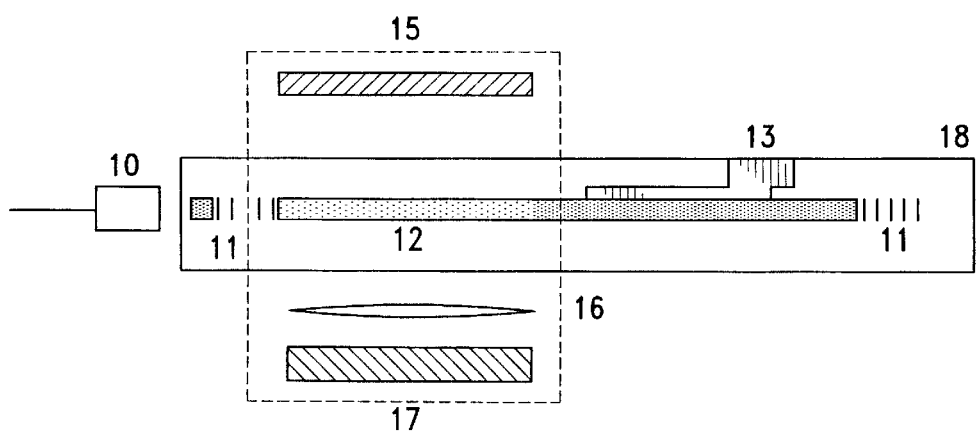

In the following, preferred embodiments of the invention are described by way of examples with reference to the drawings, wherein FIG. 1 is a top-view of a semiconductor based apparatus according to the invention, FIG. 2 shows a cross-sectional view of the apparatus in FIG. 1, FIG. 3 shows a concept of an all-polymer intracavity biosensor, and FIG. 4 shows a cross-sectional profile of an all-polymer intracavity biosensor.

Figure 5:
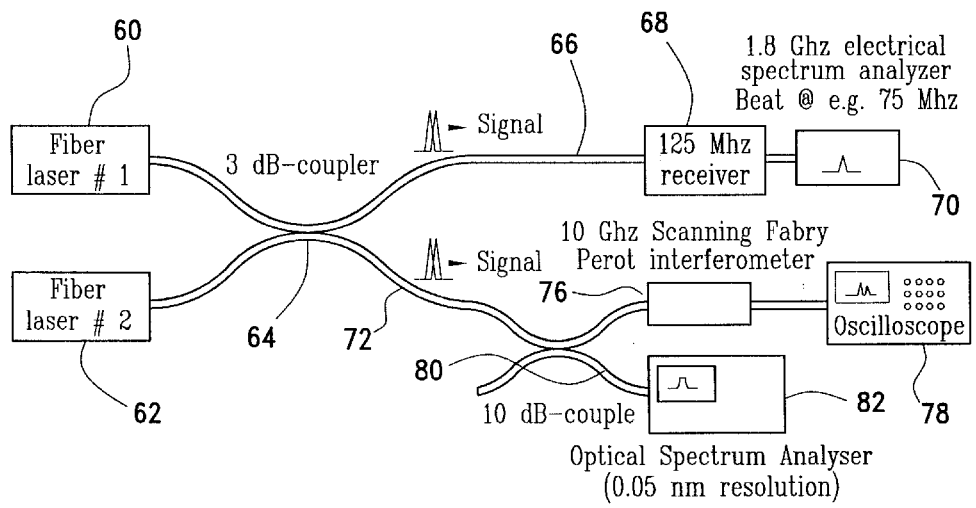
Figure 6:
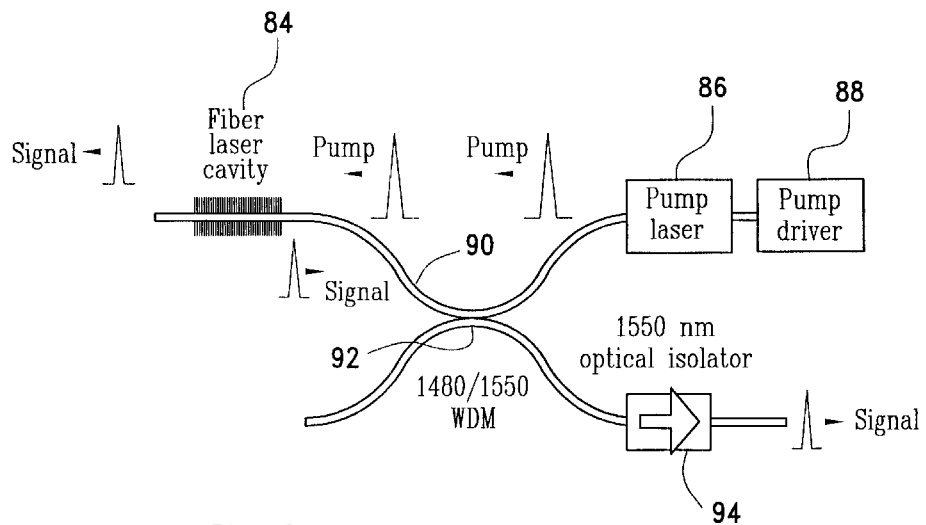

FIG. 5 shows an embodiment using two fibre lasers; and
FIG. 6 shows details of the fibre lasers of FIG. 5.

EXAMPLE 1.

Semiconductor Laser Configuration

A top-view of an apparatus according to the invention is illustrated in FIG. 1. Two closely spaced laser cavities 7, 7' are formed in a layered structure typically formed as a chip comprising a semiconductor based substrate 5 and a semiconductor based laser cavity medium 6.

The reflective end elements may be either Distributed Feed Back (DFB) 2, where the effective mirrors are distributed along the whole cavity or Distributed Bragg Reflectors (DBR) 1, where localized Bragg reflection mirrors are located at the end of the laser cavity.

A device as depicted in FIG. 1 type could readily be fabricated on the basis of methods developed for telecommunication laser cavity. GaAs, InGaAsP, or InP may form the basis for the semiconductor laser cavities 7 and 7'. In order to avoid infrared absorption GaAs (wavelength of 850 nm) is preferable, but specific applications may also tolerate a wavelength of 1300 nm or even 1500 nm.

A cross-sectional view of the semiconductor based sensor system is shown in FIG. 2. Two flow channels 8, 8' are positioned above and adjacent the two laser cavities 7, 7', respectively. The flow channels 8, 8' are defined within outer walls 9, 9' and respective upper surfaces of the cavities 7, 7'. The upper surface of one cavity 7 contain an immobilized reagent. Substance containing the chemical species to be detected is guided through the flow channels 8, 8' and the species react with the immobilized reagent in flow channel 8. Evanescent waves extend from the laser cavities 7, 7' into the flow channels 8, 8' whereby the modes of the laser cavities 7, 7' are influenced by the refractive indices of the flow channels 8, 8'. As the concentration of the species increases with time in the flow channel 8 containing the immobilized reagent, the refractive indices at the surfaces of the laser cavities 7, 7' changes differently with time.

The flow channels 8, 8' may be fabricated using convention techniques from microtechnology.

The presence of the species in the flow channel 8 may be detected by using light beating where the first and second light beam emitted from the two laser cavities, respectively, are directed towards a detector 4, e.g., using a coupling grating 3, see FIG. 1. The detector 4 and coupling grating 3 may be integrated on the same chip using conventional fabrication techniques with integrated optics.

The apparatus shown may have intrinsic conflicting properties: If the two laser cavities are very closely spaced in order to obtain the same thermal conditions, injection locking may give a highly nonlinear response. This problem could be resolved by introducing a controlled frequency offset. The time constant for the loop that controls the offset must be larger than the time constant for the refractive index changes to be measured (order of seconds). The complexity of the system is greatly enhanced by the active frequency offset.

EXAMPLE 2

Polymer Configuration

Another aspect of the invention relates to the use of polymers because it ultimately could lead to an all-polymer sensor chip 18 that can be disposed after use. The prerequisites for fulfilling this goal is that the laser cavity 12 including mirrors 11, the waveguide 14 and the microfluidics fluidics handling system 13 can be monolithically integrated onto a polymer-based chip as shown in FIGS. 3 and 4.

There are several advantages of polymer based photonic circuits. Firstly, the commercial availability of diode based pump lasers as well as the recent developments in electrically driven polymer based LED's and lasers are of great importance. Furthermore, the old problem of dye-fading in polymer matrices appears to have been solved recently, see A. Tagaya et al. in Applied Optics 36, pp. 572–578, 1997 (Ref. 14). Secondly, reliable replication methods for planar waveguide structures are now under development which will make it possible to monolithically integrate light source and waveguide. Thirdly, a polymer-based laser/waveguide/microfluid device is inherently compatible with a number of the current techniques for immobilizing the sensing layer.

The system proposed here is illustrated in FIG. 3 showing a sensor comprising a laser cavity 12, 14 made up of a first cavity and a second cavity which have a portion in common. The device is thus capable of supporting two laser beams. The characteristic area of the sensor pad is about 1cm$^2$ and the thickness is a few mm. The cavity comprises an active part or gain region 12 joined to a waveguide region 14, which is split into two arms 14a and 14b at a waveguide splitter 14c. The waveguide splitter may preferably be polarization sensitive. The laser cavity gain region 12 and the waveguide structure 14 are envisaged to be buried in a polymer (e.g. PMMA). The active part 12 could be obtained by doping with a dye or possibly a rare earth material. The pumping of a rare earth doped laser cavity in some cases may be difficult to perform in the same manner as for fibre lasers if the interaction length is too short for efficient energy transfer. Placing the polymer laser inside the cavity of a semiconductor laser may provide for the necessary energy transfer avoiding possible problems with inadequate intersection length. (The whole system would then be based on a double intracavity configuration). Single mode waveguides would provide for well-defined oscillation frequencies. As shown in FIG. 4, a dye doped laser 12 may-be pumped conventionally using an external laser source 17, a focusing element 16 and a laser cavity mirror 15.

The difference between the frequencies of the light in the two cavities is sensed by a detector 10 as the frequency of a beat component.

In order to minimize mode interaction (competition) a polarization splitter could be applied. A polarization filter in front of the detector would then be necessary in order to obtain light beating. Thus, a polarisation splitter 14c at the junction of the arms of the waveguide structure 14 will enable two mutually orthogonally polarised modes generated in the active region 12 to be separated and directed into respective arms 14a and 14b in accordance with the second aspect of the invention. One such mode may then be permitted to interact with the substance to be sensed in one of the arms.

Alternatively, the lasers may be operated at higher gain without the splitting of different polarisations.

A microfluidics system 13 is schematically indicated for passing a sample in contact with both arms 14a and 14b of the waveguide 14. One arm will then need to be provided with the sensing surface which will be adapted to interact with the sample differently from the other arm. For instance, in a biosensor, both arms may have similar sensing surfaces, only one of which is provided with a binding partner for a substance to be sensed.

The optical path length given by the product of refractive index and length determines the phase retardation. For PMMA we find that the combined effect of length change and refractive index change with temperature can be represented by a thermal expansion coefficient of approximately $5 \times 10^{-5}$.

As a further embodiment of the second aspect of the invention, the apparatus of FIG. 3 may be constructed such that the gain portion 12 of the cavity is provided by a gas laser cavity or a solid state free space transmissive (i.e. not waveguide) cavity. The arms 14a and 14b may then also form part of the gas laser cavity or may be formed solid state free space transmissive material or of waveguide material such as optical fibre. A polarization splitter is provided at the junction of the arms as described above so that respective ones of two orthogonally polarised modes generated in the gain section 12 are directed into each of the two arms. If the arms form part of the gas laser cavity, a substance to be sensed may be passed into a cell positioned within the cavity rather than being brought into proximity to a sensing surface.

EXAMPLE 3

Fibre Lasers

An embodiment using two fibre lasers as shown in FIGS. 5 and 6. The apparatus comprises a first fibre laser 60 and a second fibre laser 62 described in greater detail hereafter whose light output is passed through optical fibres to a three dB coupler 64 from which a first output fibre 66 passes to a 125 MHz receiver 68 connected to a 1.8 GHz electrical spectrum analyser 70. A second output from the coupler passes along the fibre 72 to a 10 dB coupler from which a first output signal passes along a fibre 74 to a 10 GHZ scanning Fabry-Perot interferometer 76. The interferometer is connected to an oscilloscope 78. A second output signal from the 10 dB coupler passes along a fibre 80 to an optical spectrum analyser 82. The structure of the fibre lasers 60, 62 shown as a box in FIG. 6 is shown in FIG. 7. Each has a fibre laser cavity 84 connected by an optical fibre to a pump laser 86 having a pump driver 88. The light output of the fibre is conducted via an optical fibre 90 to a pump-signal fused coupler in the form of wavelength division multiplexer (WDM) 92 and then on to a optical isolator 94 from which the signal passes to the 3 dB coupler 64.

Each fibre laser is pumped via a pump-signal fused coupler WDM 92. The pump laser may be either an 80 mW diode laser with a light output frequency of 980 nm or a 100 mw diode laser with a light output frequency of 1480 nm.

The laser 84 in its backward propagating direction is protected by the optical isolator 94. The signal laser is further protected from reflections from the forward propagating direction by an angled facet connector (FC-APC, −60 dB return loss. In order to eliminate the problem of remanant pump power mixing with the signal, the backward propagating signal from the fibre laser was used in each case. Thus no further filtering of the pump light is necessary. One of the two lasers is provided with a sensing surface in a region where the cladding of the laser fibre has been partially removed so that the surface is within the penetration depth of the evanescent field.

The two laser signals are merged using the fused fibre 3-dB coupler 64. The two laser are fabricated to have similar centre frequencies. However, due to the processes used in manufacture, the centre wavelengths may differ by up to 0.1 nm corresponding to 12 GHz. In order to match the centre frequencies so that the beat frequency lies within the band width of the detection system 125–250 MHz, the lasers can be tuned either by stretching the fibres using a micrometer resolution translation stage or by temperature, e.g. heating the laser with the lower centre wavelength (approximately 0.01 nm/K). To ease the process of frequency matching, the output from the two lasers is monitored spectrally in three levels of detail. First, the laser signals are monitored on an optical spectrum analyser with a 0.05 nm resolution. This provides a first, course, alignment platform. When the centre frequencies are within the free spectral range of the scanning Fabry-Perot interferometer, a next step of fine tuning the centre frequencies can be formed. This provides a resolution of some 10's of MHz. This is sufficient to tune the beat frequency within the 125 MHz bandwidth of the photo receiver, where final tuning can be performed.

In assessing the advantages of the methods and apparatus as illustrated above according to the invention, one needs to consider various factors including the dynamic range of the measurement (the ratio of the highest concentration of a species that can be measured to the lowest concentration), the volume of sample required (which is preferably small), and the maximum temperature gradient which can be tolerated within the sample (which is preferably large). A comparison of the method according to the invention with methods of refractive index based sensors operating as Mach-zehnder interferometers or in the manner of a commercial system (the Hewlett Packard HP 1047A Refractive Index Detector) is shown below in the following Table.

| Method | Dynamic range @ $\Delta n_{min} = 5 \times 10^{-9}$ (same reference) | Volume in $\mu l$ @ $\Delta n_{min} = 5 \times 10^{-9}$ (0.5 mg/l of saccharose in $H_2O$) | Max. relative temperature gradient |
| --- | --- | --- | --- |
| Invention | >$10^6$–$10^9$ | $10^{-4}$–$10^{-8}$ Independent of resolution | $0.5 \times 10^4$ (minimum) |
| Mach-Zehnder | $10^4$ | $10^{-4}$–$10^{-8}$ grows inversely with resolution | $0.5 \times 10^3$ (minimum) |
| HP deflection | 30 | 7 | 1 |

According to the manufacturers literature, the HP deflection method has an equivalent noise level of $\Delta n=10^{-9}$. In the above table, the volume of sample required for each method working at that level of resolution is calculated as is the dynamic range (i.e. the ratio of the largest and smallest changes in refractive index which could be sensed at that level of resolution without adjusting the instrument settings).

It is believed that the resolution achievable using the method of the invention may be as small as $\Delta n=10^{-15}$ and that would imply that in a sample volume of $10^{-9}$ $\mu l$ one would be able to detect for instance the addition or removal of one molecule from a volume of saccharose or the substitution of just 10 water molecules by sugar molecules.

Whilst the invention has been described with reference to the specific embodiments, it would be appreciated that many modifications and variations thereof are possible within the scope of the invention.

What is claimed is:

1. An apparatus for sensing the amount, concentration or presence of a substance through a change in refractive index, comprising a first laser having a laser cavity defined by a waveguide for generation of a first laser light beam and a second laser having a laser cavity defined by a waveguide for generation of a second laser light beam, the propagation of said laser light beam in said first laser cavity being characterised by a first propagation constant and the propagation of said laser light beam in said second laser cavity being characterised by a second propagation constant, the waveguide defining the first laser cavity having a sensing surface for receiving a sample of a substance to be sensed, such that the presence of said substance at said sensing surface alters the said first propagation constant and the frequency of light in said first laser beam, and means for combining said laser beams to produce beating between their respective frequencies and means for detecting a change in the said beating consequent upon a said change in said first propagation constant caused by the presence of said substance.

2. Apparatus as claimed in claim 1, wherein the laser cavities of the first laser and the second laser are separate from one another.

3. Apparatus as claimed in claim 1 or claim 2, wherein said means for combining said laser beams to produce beating between their respective frequencies and means for detecting a change in the said beating consequent upon a said change in said first propagation constant caused by the presence of said substance comprise a detector which produces an electrical output signal in response to the intensity of light incident upon it, first optical means for directing the first light beam emitted from the first laser towards the detector, and second optical means for directing the second light beam emitted from the second laser towards the detector, the first and second optical means being adapted to align the wavefronts of the first and second light beams at the detector for coherent detection of the light beams at the detector whereby the detector output signal has a component which is generated in response to the difference between the frequencies of the first and second light beams.

4. Apparatus as claimed in claim 3, wherein the first optical means comprises a first waveguide for transmission of the first light beam.

5. Apparatus as claimed in claim 4, wherein the second optical means comprise a second waveguide for transmission of the second light beam.

6. Apparatus as claimed in any preceding claim, wherein the first and second lasers are semiconductor lasers.

7. Apparatus as claimed in claim 6, wherein the first and second lasers are manufactured on a semiconductor chip.

8. Apparatus as claimed in claim 7, wherein the means for combining said laser beams to produce beating between their respective frequencies and means for detecting a change in the said beating consequent upon a said change in said first propagation constant caused by the presence of said substance are integrated in the semiconductor chip.

9. Apparatus as claimed in any one of claims 1 to 5, wherein the first and second lasers are polymer lasers.

10. Apparatus according to claim 9, wherein the lasers are manufactured on a device made of a polymer in which the means for combining said laser beams to produce beating between their respective frequencies and means for detecting a change in the said beating consequent upon a said change in. said first propagation constant caused by the presence of said substance are integrated.

11. Apparatus as claimed in any preceding claim, wherein the first and second laser cavities have cavity reflector gratings that are distributed along the length of the respective cavities.

12. The apparatus of claim 1, wherein said waveguide defining said laser cavity of said second laser is partially shared by said laser cavity of said first laser.

13. A method for sensing the amount, concentration or presence of a substance through a change of refractive index, which method comprises:

providing a first laser having a laser cavity defined by a waveguide for generation of a first laser light beam and a second laser having a laser cavity defined by a waveguide for generation of a second laser light beam, the propagation of said laser light beam in said first laser cavity being characterised by a first propagation constant and the propagation of said second laser light beam in said second laser cavity being characterised by a second propagation constant, the waveguide defining the first laser cavity having a sensing surface within an evanescent field of said first laser light beam;

receiving a sample of a substance to be sensed on said sensing surface such that the presence of said substance at said sensing surface alters the said first propagation constant and the frequency of light in said first laser light beam, combining said first and second laser light beams to produce beating between their respective frequencies and detecting a change in the said beating consequent upon a said change in said first propagation constant caused by the presence of said substance.

14. A method as claimed in claim 13 wherein said sensing surface has the ability to bind the substance to be detected.

15. A method as claimed in claim 14 wherein said sensing surface bears a specific binding partner for the substance to be detected.

16. A method as claimed in claim 15, wherein to increase detection sensitivity, the substance to be detected is bound to a refractive index change enhancing label.

17. A method as claimed in claim 16, wherein said label is a microparticle.

18. A method as claimed in claim 15 or claim 16, wherein said label is bound to the substance to be detected via a specific binding partner for said substance.

19. An apparatus for sensing the amount or presence of a substance comprising a laser having a laser cavity comprising a free space gain portion for generation of laser light in two mutually orthogonally polarized modes and a bifurcated portion comprising a pair of arms, means for splitting said laser light into two beams each of one said polarisation mode and for directing a respective beam into each of said arms of the bifurcated portion of the cavity, the light of each said polarization mode having a respective frequency, means for allowing a said substance to interact in one said arm with one of said two beams so as to alter the optical length of said arm and hence the frequency of the light of the polarization mode associated with that arm, and means for detecting said change in frequency as a change in a beat frequency component produced by beating of the two said polarization modes.

20. Apparatus as claimed in claim 19, wherein said bifurcated portion of the laser cavity provides free space transmission of light.

21. Apparatus as claimed in claim 19, wherein said bifurcated portion of the laser cavity provides waveguide transmission of light.

* * * * *